United States Patent [19]

Bird et al.

[11] Patent Number: 5,008,258
[45] Date of Patent: Apr. 16, 1991

[54] CEPHALOSPORIN DERIVATIVES

[75] Inventors: Thomas G. C. Bird, Witry-les-Reims; Frederick H. Jung, Rilly la Montagne, both of France

[73] Assignee: I.C.I.-Pharma, Gergy Cedex, France

[21] Appl. No.: 221,945

[22] Filed: Jul. 18, 1988

[30] Foreign Application Priority Data

Jul. 23, 1987 [EP] European Pat. Off. ......... 87401721.3

[51] Int. Cl.$^5$ .................. C07D 501/48; A61K 31/545
[52] U.S. Cl. .................................... 514/201; 514/202; 540/221; 540/222; 540/225
[58] Field of Search ............... 514/202, 201; 540/222, 540/225, 221

[56] References Cited

U.S. PATENT DOCUMENTS

| | | | |
|---|---|---|---|
| 4,278,793 | 7/1980 | Durckheimer | 544/207 |
| 4,678,781 | 7/1987 | Jung | 540/227 |

FOREIGN PATENT DOCUMENTS

| | | |
|---|---|---|
| 182210 | 5/1986 | European Pat. Off. |
| 186187 | 7/1986 | European Pat. Off. |
| 238060 | 8/1987 | European Pat. Off. |
| 241901 | 10/1987 | European Pat. Off. |
| 1399086 | 6/1975 | United Kingdom |

*Primary Examiner*—Nicholas S. Rizzo
*Attorney, Agent, or Firm*—Cushman, Darby & Cushman

[57] ABSTRACT

Cephalosporin compounds having as a 3-substituent the group:

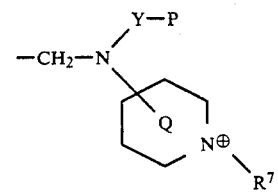

wherein Y represents a bond, optionally substituted alkylene or —CH$_2$CH$_2$NHCO—, P is a benzene ring substituted by groups W and Z ortho with respect to one another wherein W is hydroxy or an in vivo hydrolyzable ester thereof, Z is hydroxy, an in vivo hydrolyzable ester thereof, carboxy, sulpho, hydroxymethyl, —NHSO$_2$CH$_3$ or NHCONH$_2$, Q is a mono- or bicyclic ring system substituted by R$^7$ wherein R$^7$ is hydrogen or a range of groups and ring Q is optionally further substituted; are described as antibacterial agents. Processes for their preparation and their methods of use are described.

7 Claims, No Drawings

CEPHALOSPORIN DERIVATIVES

This invention relates to cephalosporin derivatives which have antibacterial activity.

In this specification (including in the claims) the term cephalosporin derivative, irrespective of the actual derivation of any individual such compound, includes the cephalosporins and the 7α-methoxy, 7α-formamido and 1-oxide derivatives thereof (wherein the 1-oxides may have the R or S configuration) and analogues of the above compounds wherein the sulphur atom or sulphinyl group at the 1-position is replaced by an oxygen atom or a methylene group.

The cephalosporin derivatives referred to herein are generally named in accordance with the "cephem" nomenclature and numbering system proposed in J. Amer. Chem. Soc. 1962, 84,3400.

Formulae referred to by roman numerals are set out hereinafter.

According to the invention there is provided a cephalosporin derivative having antibacterial activity characterised in that the substituent at the 3 position has the formula I in which:

Q represents a 5 to 10 membered mono- or bicyclic heterocyclic ring system bonded to the amino nitrogen atom via a carbon atom and containing, in addition to the positively charged nitrogen atom, 0 to 5 further heteroatoms selected from nitrogen, oxygen and sulphur and being optionally substituted:

on a carbon atom or atoms available for substitution by 1,2 or 3 groups R5 wherein R5 is halogen, (1-6C)alkyl, carboxy, (2-6C)alkoxycarbonyl, (2-6C)alkoxycarbonyl(1-4C)alkyl, (1-6C)alkyl, (1-6C)-alkoxy, (1-6C)alkylthio, cyano, (1-4C)cyanoalkyl, amino, (1-6C)alkylamino, (2-8C)dialkylamino, phenyl (1-4C)alkylamino, nitrophenyl(1-4C)alkylamino, heteroaryl(1-4C)alkylamino (wherein heteroaryl is a 5- or 6-membered ring containing 1, 2 or 3 heteroatoms selected from nitrogen, oxygen and sulphur), (3-6C)alkenylamino, amino(1-6C)alkylamino, (1-6C)alkoxy(1-6C)alkylamino, hydroxy(1-6C)alkylamino, hydroxy, mercapto, carbamoyl, (2-6C) alkylcarbamoyl, (3-10C)dialkylcarbamoyl, phenylthio and heteroarylthio (wherein heteroaryl is as hereinbefore defined), wherein when more than one group R5 is present these may be the same or different;

on an uncharged nitrogen atom available for substitution by a group R6 wherein R6 is (1-6C)alkyl, phenyl or benzyl;

R7 is hydrogen, (1-6C)alkyl (optionally substituted by carboxy, (1-6C)alkoxycarbonyl, carbamoyl, mono- or di-(1-4C)alkylcarbamoyl, hydroxy, (1-4C)alkoxy, amino, mono- or di-(1-4C)alkylamino, (1-4C)alkanoyl, benzoyl, cyano, carboxyaminocarbonyl, (1-6C)alkoxycarbonylaminocarbonyl, (1-4C)alkoxy(2-4C)alkoxy or phenyl), (1-6C)alkoxy, phenyl(1-6C)alkoxy, amino, (1-6C)alkylamino, (3-6C)cycloalkyl, (3-6C)cycloalkenyl, cyano(3-6C)cycloalkenyl, (2-6C)alkenyl (optionally substituted by (1-6C)alkyl, halogen, cyano, carbamoyl, mono- or di-(1-4C)alkylcarbamoyl, piperidinocarbonyl or morpholinocarbonyl), 2-ureidoethyl, 2-thioureidoethyl, 2-(thioacetylamino)-ethyl, sulphamoyl, 2-amino-2-carboxyethyl, acetylaminomethyl, phthalimidomethyl, 4-5 dihydro-imidazol-2 ylmethyl, 3,4,5,6 tetrahydropyrimidin-2-ylmethyl, 2-(1,2,3,6-tetrahydro-2,6-dioxopurin-7-yl)ethyl, 2-hydroxyiminopropyl (syn or anti) [(1-4C)alkoxyimino]propyl (syn or anti) or phenyl, or R7 is of the formula —(CH$_2$)$_2$—$\overset{+}{N}$R8R9R10 in which R8, R9 and R10 are 1-4C)alkyl, or R7 is of the formula —(CH$_2$)$_s$—R11 in which s is 0-2 and R11 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C)alkyl]tetrazole, furan, thiophene, pyrrole, 1-[(1-4C)alkyl]pyrrole, oxazole, thiazole, imidazole, 1-[1-4C)alkyl]imidazole, isoxazole, isothiazole, pyrazole, 1,2,3-thiadiazole, 1-[(1-4C)alkyl]pyrazole, benzfuran, benzthiophene, indole, oxindole, 1-[(1-4C)alkyl]indole, benzoxazole, benzthiazole, benzimidazole, 1-[(1-4C)alkyl]benzimidazole, or 3,4-dihydro-4-oxo-2Hbenzo[e]oxazine (each of these ring systems being linked to (CH$_2$)$_s$ through carbon and each ring system being optionally substituted by halogen, (1-6C)alkyl, (1-4C)haloalkyl, (3-6C)cycloalkyl, (3-6C)cycloalkyl(1-4C)alkyl, (2-6C)alkenyl, carboxy, (2-6C)alkoxycarbonyl, (1-6C)alkoxy, cyano, (2-6C)-cyanoalkenyl, carbamoyl, mono-or di-(1-4C)alkyl-carbamoyl, (1-4C)alkanoylamino, guanidino, hydroxy, nitro or amino), or R7 is 2 guanidino-thiazol-4-ylmethyl, hydroxybenzoylmethyl, 2-thenyl, 2-imidazolylmethyl or cinnamyl (each optionally substituted by halogen, (1-6C)alkyl, hydroxy, (1-4C)alkoxy, carboxy, (2-6C)-alkoxycarbonyl, nitro or carbamoyl), or R7 is —(CH$_2$)$_t$NHCOR12 or —(CH$_2$)$_t$S(O)$_u$—R12 in which t is 1-6, u is 0, 1 or 2 and R12 is (1-6C)alkyl or (1-6C)alkoxy, or R7 is of the formula (CH$_2$)$_2$N=CR13NR14R15 or —(CH$_2$)$_v$C(=NR13)NR14R15 or a tautomer thereof in which v is 1-6 and R13, R14, R15 are hydrogen or (1-4C)alkyl, (wherein when R7 is or contains a phenyl group, the phenyl group is optionally substituted by 1 or 2 groups selected from halogen, (1-6C)alkyl, (1-6C)alkoxy, amino, carboxy, nitro, carbamoyl, cyano, trifluoromethyl, aminomethyl, (1-4C)alkanoyl, (1-4C)-alkanoylamino, halo(1-4C)alkyl, (2-6C)alkoxycarbonyl, mono- or di-(1-4C)alkylcarbamoyl, mesyl, vinyl, sulpho, sulphamoyl or mono- or di(1-4C)alkylsulphamoyl)

or when the positively charged nitrogen atom occurs at the junction between fused rings R7 is absent;

Y is straight or branched (1-6C)alkylene optionally substituted by cyano, carboxy, (1-4C)alkoxycarbonyl, nitro, halogen, carbamoyl, mono- or di-(1-4C)alkylcarbamoyl or trifluoromethyl; or Y is —CH$_2$CH$_2$NHCO— or a bond;

P represents:

(i) a benzene ring optionally fused to a further benzene ring (so forming a naphthyl group) or to a 5 or 6 membered heterocyclic aromatic group containing 1, 2 or 3 heteroatoms selected from nitrogen, oxygen and sulphur and said ring system substituted by groups W and Z which are ortho with respect to one another wherein W is hydroxy or an in vivo hydrolysable ester and Z is hydroxy, an in vivo hydrolysable ester thereof, carboxy, sulpho, hydroxymethyl,—NHSO$_2$CH$_3$ or —NHCONH$_2$;

(ii) a group of formula II; or (iii) a group of formula III and tautomers thereof wherein M represents oxygen or NR$^b$ wherein R$^b$ represents hydrogen or (1-4C) alkyl;

ring system p optionally being further substituted by (1–4C)alkyl, halogen, hydroxy, cyano, trifluoromethyl, nitro, amino, mono- or di-(1–4C)alkylamino, formyl, (1–4C)alkanoyl, (1–4C)alkoxy, (1–4C)alkylthio, (1–4C)alkanoyloxy, carbamoyl or mono- or di(1–4C)alkylcarbamoyl;

and the N-oxides thereof where chemically possible;

and the salts formed with acids and bases which afford pharmaceutically acceptable anions and cations respectively.

A particular group of compounds according to the invention are those of formula Ia and salts thereof wherein Q, Y, and P are as hereinbefore defined and in which X is sulphur, oxygen, methylene or sulphinyl (R or S configuration) and R1, R4 and A are groups known in the art of antibacterial cephalosporins.

R1 is for example 2-aminothiazol-4-yl or 2 aminooxazol-4-yl each optionally substituted in the 5-position by fluorine, chlorine or bromine, or R1 is 5 amino-isothiazol-3-yl, 5 amino-1,2,4-thiadiazol-3-yl, 3-aminopyrazol-5 yl, 3-aminopyrazol-4-yl, 2-aminopyrimidin-5yl, 2-aminopyrid-6-yl, 4 aminopyrimidin-2 yl, 2-amino-1,3,4-thiadiazol-5yl or 5-amino-1-methyl-1,2,4-triazol-3-yl.

A is for example of the formula =N.0.R2 (having the syn configuration about the double bond) wherein R2 is hydrogen, (1–6C)alkyl, (3–8C)cycloalkyl, (1–3C)alkyl(-3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, di(1–4C)alkyl-carbamoyl(1–4C)alkyl, (1–4C)haloalkylcarbamoyl (1–4C) alkyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkane-sulphonyl(1–4C)alkyl, amino(2–6C)alkyl, azido(2–6C)alkyl, ureido(-2–6C)alkyl, (1–4C)alkylamino(1–6C)alkyl, (2–8C)dialkylamino(2–6C) alkyl, (1–5C)cyanoalkyl, 3-amino 3-carboxypropyl, 2 (amidino)ethyl, 2-(amidinothio)ethyl, 2-(N-aminoamidinothio)ethyl, tetrahydropyran-2-yl, thietan-3 yl, 2-oxopyrrolidinyl, or 2 oxotetrahydrofuranyl, or -R2 may be of the formula IV in which q is 1 or 2 and R24 and R25 are hydrogen or (1–4C)alkyl, or -R2 may be of the formula V in which r is 0–3, R32 is hydrogen, (1–3C)alkyl or methylthio, R33 is hydrogen, (1–3C)alkyl, (3–7C)cycloalkyl, cyano, carboxy, (2–5C)carboxyalkyl or methanesulphonylamino, or R32 and R33 are joined to form, together with the carbon to which they are attached, a (3–7C)carbocyclic ring, and R34 is hydroxy, amino, (1–4C)alkoxy, (1–4C) alkylamino, or of the formula NHOR35 in which R35 is hydrogen or (1–4C)alkyl;

or A may be of the formula =CH.R3 wherein R3 is hydrogen, halogen, (1–6C)alkyl, (3–7C)cycloalkyl, (2–6C)alkenyl, (3–7C)cycloalkenyl, phenyl or benzyl.

R4 is suitably hydrogen, methoxy or formamido;

It is to be understood that in the above formula I and throughout this specification, the illustrated stereochemistry of the ceph-3 em nucleus, and its optional modifications at the 1-position, is the absolute configuration. It is also to be understood that, since ring Q contains a quaternary nitrogen, the compounds of the invention will normally exist in zwitterionic form, involving the quaternary nitrogen and the carboxy group. When the compound of the invention contains further acidic or basic substituents, it is to be understood that the possibility of a double zwitterionic form of the compound will arise. Alternatively, exogenous anions or cations may be included, to form pharmaceutically-acceptable base-addition or acid-addition salts, as defined above.

It will also be understood that references herein to a particular nitrogen atom bearing a positive charge and to other nitrogen atoms being uncharged are made for the sake of convenience in defining the compounds of the invention and that all possible resonance hybrids of the structures so defined are included within the scope of the invention.

A particular meaning for R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2 bromoethyl, 2-hydroxyethyl, 3-hydroxypropyl, 2-methoxyethyl, 2 ethoxyethyl, 2 methylthio-ethyl, 2-methanesulphinylethyl, 2-methanesulphonyl-ethyl, 2-aminoethyl, 3-aminopropyl, 2-methylamino ethyl, 2 dimethylaminoethyl, cyanomethyl, 2-cyanoethyl, azidomethyl, 2-azidoethyl, ureidomethyl, 3 amino 3-carboxypropyl, 2-(amidino)ethyl, 2-(N-aminoamidino)-ethyl, tetrahydropyran-2-yl, thietan-3 yl, 2-oxopyrrolidinyl or 2-oxotetrahydrofuran-3-yl, or, when R2 is of the formula IV in which q is 1 or 2, a particular meaning for R2 is when R24 and R25 are hydrogen or methyl, or, when R2 is of the formula V, a particular meaning for R2 is when r=0 and R32 is hydrogen, methyl or methylthio, R33 is hydrogen, methyl, cyclopropyl, cyclobutyl, cyclopentyl, cyclohexyl, cyano, carboxy, carboxymethyl, 2 carboxyethyl or methanesulphonylamino, or when R32 and R33 are joined to form, together with the carbon to which they are attached, a cyclopropane, cyclobutane, cyclopentane, cyclohexane or cycloheptane ring and R34 is hydroxy, amino, methoxy, ethoxy, methylamino, ethylamino, or of the formula NHOR35 in which R35 is hydrogen, methyl, or ethyl.

Preferably $R^2$ is (1–6C)alkyl for example methyl or ethyl, 1-carboxycyclobutyl, 1-carboxycyclopentyl or 2 carboxyprop-2-yl.

Particular meanings for R3 are hydrogen, methyl or chlorine.

A particular meaning for R4 is hydrogen.

A particular ring system represented by ring Q is a 5 or 6 membered ring containing NR7 and 0 to 3 further heteroatoms selected from nitrogen, oxygen and sulphur and optionally fused on an available carbon-carbon or carbon-nitrogen bond to a benzene ring or a ring of formula (VI) wherein T, U and V are selected from oxygen, sulphur, nitrogen, carbon, —NH— and —CH—optionally substituted where possible, by groups R5 and R6 as defined above.

Further particular ring systems represented by ring Q are those of formulae VII–XIV wherein one of D, D', E and E' represents NR7 and the remainder represent uncharged nitrogen atoms.

Still further particular ring systems represented by ring Q are those of formula XV and XVI wherein R37 represents hydrogen or a group R6 as hereinbefore defined, and XVII–XXI.

Still further particular ring systems represented by ring Q are those of formulae XXII (wherein T is as hereinbefore defined) and XXIII-XXVI.

Any of rings VII XXVI may optionally be substituted, where possible, by one or more groups R5 and R6 as hereinbefore defined.

When ring Q represents a 5 or 6 membered ring as defined above a particular meaning therefor is pyridine or pyrimidine, optionally fused to a benzene ring or a ring of formula VI which is a thienyl group.

Particular meanings for the group R5 are fluorine, chlorine, bromine, methyl, ethyl, n-propyl, isopropyl, carboxy, methoxycarbonyl, ethoxycarbonyl, methoxycarbonylmethyl, ethoxycarbonylmethyl, methoxy, ethoxy, methylthio, ethylthio, cyano, cyanomethyl, 2 cyanoethyl, amino, methylamino, ethylamino, isopropylamino, dimethylamino, benzylamino, nitrobenzylamino, allylamino, 2-aminoethylamino, 2-methoxyethylamino, 2-hydroxy ethylamino, hydroxy, mercapto, carbamoyl, methyl-carbamoyl, ethylcarbamoyl, dimethylcarbamoyl, phenylthio and heteroarylthio in which the heteroaryl ring is a furan, thiophene, imidazole, thiazole, pyrazole, thiadiazole, pyridine, pyrimidine, pyrazine or pyridazine.

Particular meanings for the group R6 are methyl, ethyl, n-propyl, isopropyl, phenyl or benzyl.

Particular meanings for R37 are hydrogen and the particular meanings given above for R6.

Particular meanings for the group R7 are hydrogen, methyl, ethyl, n-propyl, isopropyl, t-butyl, carboxymethyl, 2 carboxyethyl, methoxycarbonylmethyl, 2 methoxycarbonylethyl, carbamoylmethyl, 2-carbamoylethyl, mono- and dimethylcarbamoylmethyl, hydroxymethyl, 2-hydroxyethyl, methoxymethyl, 2 methoxyethyl, aminomethyl, 2-aminoethyl, 2-methylaminoethyl, 2-dimethylaminoethyl, acetylmethyl, propionylmethyl, benzoylmethyl, cyanomethyl, 2 cyanoethyl, 3-cyanopropyl, carboxyaminocarbonylmethyl, 2-(carboxyaminocarbonyl)ethyl, methoxycarbonyl-aminocarbonylmethyl, 2-(methoxycarbonyl-aminocarbonyl)ethyl, 2-methoxyethoxymethyl, benzyl, 2 phenethyl, methoxy, ethoxy, benzyloxy, 2 phenylethoxy, amino, methylamino, ethylamino, cyclopropyl, cyclobutyl, cyclopentyl, cyclopentenyl, 3 cyanocyclopent-2 enyl, vinyl, allyl, 2,4 pentadienyl, 3-chloroallyl (cis and trans), 3-cyanoallyl, 2-ureidoethyl, 2-thioureidoethyl, 2-thioacetylamino)ethyl, sulphamoyl, 2 amino-2-carboxyethyl, acetylaminomethyl, phthalimidomethyl, 4,5-dihydroimidazol-2-ylmethyl, 3,4,5,6 tetrahydropyrimidin-2-ylmethyl, 2-(1,2,3,6-tetrahydro-2,6-dioxopurin-7-yl)-ethyl, 2-hydroxyiminopropyl (syn or anti), 2 (methoxyimino)propyl (syn or anti), 2-(ethoxyimino)propyl (syn or anti) or phenyl, or where R7 is of the formula $(CH_2)_2$-$NR8R9R10$ in which R8, R9 and R10 are methyl or ethyl, or where R7 is of the formula $(CH_2)s$—R11 in which s is 0–2 and R11 is pyridine, pyridazine, pyrimidine, pyrazine, 1,2,5,6-dihydro-5,6-dioxo-1,2,4-triazine, 2-(methyl or ethyl)-1,2,5,6-dihydro-5,6-dioxo-1,2,4-triazine, 1-(methyl or ethyl)tetrazole, furan, thiophene, pyrrole, 1-(methyl or ethyl)pyrrole, oxazole, thiazole, imidazole, 1-(methyl or ethyl)imidazole, isoxazole, isothiazole, pyrazole, 1-(methyl or ethyl) pyrazole, 1,2,3-thiadiazole, benzfuran, benzthiophene, indole, 1-(methyl or ethyl)indole, oxindole, benzoxazole, benzthiazole, benzimidazole, 3,4-dihydro-4 oxo-2H-benzo[e]oxazine, 1-(methyl or ethyl)benzimidazole, each of these ring systems being linked to $(CH_2)s$ through carbon and each ring system being optionally substituted by fluorine, chlorine, bromine, methyl, ethyl, n-propyl, isopropyl, trifluoromethyl, cyclopropylmethyl, formamido, carboxy, methoxycarbonyl, ethoxycarbonyl, methoxy, ethoxy, cyano, 3-cyanoallyl, carbamoyl, methylcarbamoyl, dimethylcarbamoyl, hydroxy, guanidino, nitro or amino, or where R7 is 2 guanidinothiazol-4 ylmethyl, 3-hydroxybenzoylmethyl, 2 thenyl, 2 imidazolylmethyl or cinnamyl each optionally substituted by fluorine, chlorine, bromine, methyl, ethyl, n-propyl, isopropyl, hydroxy, methoxy, ethoxy carboxy, methoxycarbonyl, ethoxycarbonyl or carbamoyl, or where R7 is of the formula —$(CH_2)_t$—N-H—CO—R12 or $(CH_2)_t$—$S(O)_s$—R12 in which t is 1–6, s is 0, 1 or 2 and R12 is methyl, ethyl, methoxy or ethoxy, or where R7 is of the formula $(CH_2)_2N=CR13NR14R15$ or $(CH_2)_2C(=NR13)NR14R15$ in which R13, R14 and R15 are hydrogen or methyl, (wherein when R7 is or contains a phenyl group the phenyl group is optionally substituted by 1 or 2 groups selected from fluorine, chlorine, bromine, amino, carboxy, nitro, carbamoyl, cyano, trifluoromethyl, aminomethyl, methyl, ethyl, methoxy, ethoxy, acetyl, acetamido, methoxycarbonyl, ethoxycarbonyl, methylcarbamoyl, dimethylcarbamoyl, diethylcarbamoyl, mesyl and sulpho).

Particular meanings of Y include $C_{1-6}$ alkylene for example methylene(—$CH_2$), ethylene(—$CH_2CH_2$—) and propylene (—$CH_2CH_2CH_2$—). Preferably Y represents methylene, ethylene, $CH_2CH_2NHCO$— or a bond so that ring P is directly linked to the 3'-amino group.

Preferably P is a benzene ring substituted by groups W and Z and optionally further substituted by halo for example bromo. W is hydroxy or an in-vivo hydrolysable ester thereof. In-vivo hydrolysable esters are those pharmaceutically acceptable esters that hydrolyse in the human or animal body to produce the parent hydroxy compound. Such esters can be identified by administering e.g. intravenously to a test animal the compound under test and subsequently examining the test animal's body fluids. Suitable in-vivo hydrolysable esters include $C_{1-6}$ alkanoyloxy for example acetoxy, propionyloxy, pivaloyloxy, $C_{1-4}$ alkoxycarbonyloxy for example ethoxycarbonyloxy, and phthalidyloxy. Preferably Z is hydroxy or an in-vivo hydrolysable ester thereof. Conveniently W and Z have the same value and are both hydroxy or both in-vivo hydrolysable esters, for example they are both acetoxy or pivaloyloxy.

A particular acid which affords a pharmaceutically-acceptable anion is, for example, hydrochloric, hydrobromic, phosphoric, sulphuric, citric or maleic acid.

A particular base which affords a pharmaceutically acceptable cation is, for example, a base containing an alkali metal, (e.g. sodium or potassium) or an alkaline earth metal (e.g. calcium or magnesium), or a primary, secondary or tertiary organic amine (e.g. triethylamine, morpholine, N methylpiperidine, N-ethylpiperidine, procaine, dibenzylamine or N,N'-dibenzylethylenediamine), or other amine which has been used to form salts with cephalosporins.

The compounds of formula I may be prepared by the following processes, which form further aspects of the invention, and in which the groups R1, A, R2, R3, R4, R5, Q, P, X and Y have the meanings already assigned to them.

(A) Reaction of a cephalosporin derivative having a group of formula —CH$_2$L (wherein L is a leaving group) at the 3-position with a nucleophilic compound serving to form the group of formula I.

A nucleophilic compound serving to form the group of formula I may be for example a compound of formula XXVII or XXVIII. Particular meanings for the leaving group L include C$_{1-4}$ alkanoyloxy (e.g. acetoxy) and halo (e.g. chloro or iodo).

(B) Reaction of a cephalosporin derivative having a group —CH$_2$NH—Y—P at the 3 position with a compound of formula XXIX (wherein R39 is a leaving group).

Particular meanings for the leaving group R39 include (1–4C)alkylthio (eg methylthio), (1–4C)-alkylsulphoxy (eg methylsulphoxy) and halogen (eg chlorine)

(C) Reaction of a cephalosporin derivative having a group of formula XXX at the 3 position with a compound of formula XXXI wherein J and K in the above formulae XXX and XXXI are such that reaction takes place to form the link —Y— between ring P and the amino nitrogen atom. For example, the compound of formula XXX may be a compound wherein J=hydrogen or a deprotonated form of such a compound, or J may be —CH$_2$CH$_2$NH$_2$ and K may be —COCl such that groups J and K react to form a link of formula —CH$_2$CH$_2$NHCO— between P and the amino nitrogen atom.

(D) (Where a compound in which W and Z are hydroxy groups is desired) deprotection of a corresponding compound in which hydroxyl groups W and Z are protected by hydroxy protecting groups.

(E) (Where a compound in which W and Z are in vivo hydrolysable ester groups is required) reaction of a compound in which W and Z are hydroxy groups with an appropriate acid or a reactive derivative thereof. Particular in vivo hydrolysable ester groups are (1–4C)alkanoyloxy groups.

A reactive derivative of a (1–4C)alkanoic acid may be for example the acid chloride.

(F) (Where a compound of formula I having a free carboxyl group is required) deprotection of a corresponding compound containing a protected carboxy group.

(G) (Where a salt of the compound of formula I is required) reaction of a compound of formula I having a free acidic or basic group with a pharmaceutically acceptable base or acid.

(H) (Where a compound of formula I having a free amino group is required) deprotection of a corresponding compound having a protected amino group.

(I) (Where a compound of formula I which is a cephalosporin 1-oxide is required) oxidation of the corresponding cephalosporin compound by conventional means, (J) (Where a compound of formula I having S at the 1-position is required) reduction of the corresponding 1-oxide by conventional means.

(K) Introduction or modification of a group at the 7-position of the cephalosporin derivative. For example, a compound of formula Ia may be prepared by one of the following processes.

(K)(a) Reaction of a compound of formula XXXII with an acid of formula XXXIII or a reactive derivative thereof.

(K)(b) Reaction of a compound of formula XXXIV with a compound of formula R2—O—NH$_2$.

(K)(c) (Where a compound of formula Ia wherein R2 is other than hydrogen is required) reaction of a compound of formula Ia wherein R2 is hydrogen with a compound of formula R40-R41 wherein R40 is a leaving group and R41 has one of the meanings given for R2 other than hydrogen.

(K)(d) Formation of a group R1 by cyclisation of an appropriate precursor therefor.

For example a 2 aminothiazol-4-yl group may be formed by reacting a compound of formula XXXV (wherein R42 is a leaving group) with a compound of formula XXXVI (wherein R43 is amino or protected amino) followed by removal of the amino protecting group if present. Certain cephalosporin compounds used as starting materials in the preparation of the compounds of the present invention are described in our published European Patent Applications Nos. 127992 and 164944, or may be prepared by methods analogous to those described in the said applications.

In a further aspect the invention provides, as starting materials for the manufacture of antibiotic compounds of formula I, the following novel compounds as defined above:

1. A compound of formula XXXII and derivatives thereof wherein the 7-amino group is protected;
2. A compound of formula XXXIV;
3. A compound of formula XXXV;

The compounds of the formulae XXXII, XXXIV or XXXV or protected derivatives thereof are prepared in a manner analogous to that described for the preparation of the compounds of the formula Ia.

When reference is made to protecting groups being present at any position in the compounds described herein such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol silanol or stannanol (the said alcohol, phenol, silanol or stannanol preferably containing 1-20 carbon atoms).

Examples of carboxyl protecting groups include straight or branched chain (1–12C)alkyl groups (eg isopropyl, t-butyl); halo lower alkyl groups (eg 2 iodoethyl, 2,2,2-trichloroethyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxy-carbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2 6C)alkenyl groups (eg allyl and vinylethyl).

Methods particularly appropriate for the removal of carboxyl protecting groups include for example acid-, bas ®-, metal- or enzymically catalysed hydrolysis.

Examples of hydroxyl protecting groups include lower alkoxycarbonyl groups (eg t-butoxycarbonyl); halo lower alkoxycarbonyl groups (eg 2-iodoethoxy carbonyl, 2,2,2-trichloroethoxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

A (1-4C)alkanoyl group (eg acetyl) may also be regarded as a hydroxyl protecting group in the context of the compounds of the invention in that compounds of formula I in which W and/or Z represent (1-4C)-alkanoyloxy (eg acetoxy) groups (which are in themselves compounds of the invention) may readily be converted by conventional means into the corresponding hydroxy compounds.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; acyl (eg alkoxycarbonyl and aralkoxycarbonyl eg t-butoxycarbonyl and benzyloxycarbonyl); trialkylsilyl (eg trimethylsilyl and t-butyldimethylsilyl); alkylidene (eg methylidene); benzylidene and substituted benzylidene groups; and the phthalimido group.

As noted above the cephalosporin derivatives of the invention have antibacterial properties. Thus they may be useful antibacterial agents, having a broad spectrum of activity in vitro against standard laboratory microorganisms, both Gram-negative and Gram-positive, which are used to screen for activity against pathogenic bacteria The antibacterial spectrum and potency of a particular compound may be determined in a standard test system, The compounds have particularly high activity in vitro against strains of *Pseudomonas aeruginosa*.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. A number of compounds were administered to mice at doses in excess of those required to afford protection against bacterial infections, and no overt toxic symptoms or side effects attributable to the administered compounds were noted.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2 acylamino-3 substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.1 to 50 g., and preferably 0.5 to 10 g., of the cephalosporin derivative, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated by, but not limited to, the following Examples, in which the following abbreviations are used:

AcOH = acetic acid
DMF = dimethylformamide
DMSO = dimethylsulphoxide
EtOAc = ethyl acetate
EtOH = ethanol
HPLC = high performance liquid chromatography
MeOH = methanol
NMR = nuclear magnetic resonance spectroscopy
TEA = Triethylamine
TFA = trifluoroacetic acid The NMR spectra are taken at 90 MHz and are quoted in terms of delta values in parts per million (ppm) with reference to tetramethylsilane (delta = 0).

In the quotation of NMR data s = singlet, d = doublet, t = triplet, q = quartet, m = multiplet and br = broad J = coupling constant.

Reference may be made to our published European Patent Applications Nos. 127992 and 164944 for de-

EXAMPLE 1

To a solution of 7 [2-(2-aminothiazol-4 yl) 2-(Z)-ethoxyiminoacetamido]-3-(3,4-diacetoxybenzyl)-aminomethylceph-3- em-4-carboxylic acid (500mg) and 1-methyl-4 methylthiopyrimidinium tetrafluoroborate (250mg) in DMF (8ml) was added dropwise triethylamine (0.165ml) and the mixture stirred for 16 hours. The solvent was evaporated, the residue (di-acetoxy compound) taken up in $H_2O$ (40ml) and MeOH (10ml) and the pH adjusted to and maintained at 8.5. After 4h the mixture was acidified to pH2.0 with aqueous HCl (2N) evaporated to dryness and purified on a Diaion HP 20 SS resin column using MeOH/$H_2O$ mixtures of increasing proportions of MeOH and containing AcOH (1%). Evaporation and freeze-drying of correct fractions yielded the product as detailed in Tables I and II.

EXAMPLES 2-21

The general process of Example 1 was used to prepare the compounds of Examples 2=21 as detailed in Tables I and II.

TABLE I

[Structure of cephalosporin compound with $R^1$ and $R^2$ substituents]

| Example | −R1 | −R2 | Yield | Footnotes |
|---|---|---|---|---|
| 1 | −Et | pyridinium-N-CH3 | 32 | |
| 2 | −Et | thiazolo-pyridinium with S | 16 | |
| 3 | −Et | pyridinium-N-CH2-C6H4-CONH2 | 28 | |
| 4 | −Et | pyridinium-N-CH2-C6H4-NO2 | 33 | |
| 5 | −Et | pyridinium-N-CH3 | 18 | 1 |
| 6 | −CH2CF3 | pyridinium-N-CH3 | 16 | 1 |
| 7 | −CH2CF3 | pyridinium-N-CH2-C6H4-CONH2 | 4 | |

TABLE I-continued

Structure: cephalosporin core with 7-position [2-(2-aminothiazol-4-yl)-2-(OR¹-oxyimino)acetamido] group and 3-position CH₂–N(R²)(CH₂-3,4-dihydroxyphenyl) substituent, COO⁻ at C-4.

| Example | —R1 | —R2 | Yield | Footnotes |
|---|---|---|---|---|
| 8 | —C(CH₃)₂CO₂H | N-methylpyrazinium-CH₂– | 17 | |
| 9 | —C(CH₃)₂CO₂H | N-(4-carbamoylbenzyl)pyrazinium– | 9 | |
| 10 | —CH(CH₃)CO₂H | N-methylpyrazinium-CH₂– | 30 | |
| 11 | —CH(CH₃)COOH | N-(4-carbamoylbenzyl)pyrazinium– | 16 | |
| 12 | —CH₂COOH | N-methylpyrazinium-CH₂– | 12 | |
| 13 | —CH₂COOH | N-(4-carbamoylbenzyl)pyrazinium– | 8 | |
| 14 | —CH₂COOH | N-(4-nitrobenzyl)pyrazinium– | 8 | |
| 15 | —CH₂CF₃ | N-allylpyridinium– | 5 | 2,3 |
| 16 | —CH₂CF₃ | N-(1,2,3-thiadiazol-4-ylmethyl)pyridinium– | 5 | 2,4 |
| 17 | —CH₂CF₃ | N-(methylthiomethyl)pyridinium– | 5 | 2,4 |
| 18 | —CH₂CH₃ | N-(1,2,3-thiadiazol-4-ylmethyl)pyridinium– | 4 | 2,5 |

TABLE I-continued

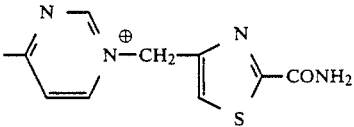

| Example | —R1 | —R2 | Yield | Footnotes |
|---|---|---|---|---|
| 19 | —CH₂CH₃ | (structure: pyridinium-CH₂-thiazole-CONH₂) | 14 | 2,4 |
| 20 | —CH₂CH₃ | (structure: pyridinium-CH₂-thiazole-CN) | 13 | 2,4 |
| 21 | —CH₂CH₃ | (structure: pyridinium-CH₂-thiazole-C(NH₂)=NH₂) | 21 | 4 |

Footnote
1. In the preparation of these compounds the reaction was stopped after the first evaporation of solvent and the subsequent steps omitted giving the compound in the form of the 2,3-diacetoxy derivative.
2. In the preparation of these compounds the intermediate diacetoxy compound was purified on Diaion HP20SS resin prior to deprotecting at pH8.5.
3. Reaction time 1 hour 15 minutes.
4. Reaction time 2 hours 30 minutes.
5. Reaction time 3 hours 30 minutes.

TABLE II

NMR data for the compounds of Examples 1-21 in $DMSOd_6 + CD_3CO_2D + TFAd$.

| Example No. | |
|---|---|
| 1 | 1.3(t,3H); 3.2–3.6(m,2H); 3.85(s,3H); 4.2 (q,2H); 4.6–4.8 (m,2H); 4.8–5.0(m,2H); 5.1(d,1H); 5.8(d,1H); 6.3–6.9(m,3H); 7.0 (s,1H); 7.15(d,1H); 8.3(d,1H); 8.8(s,1H). |
| 2 | 1.3(t,3H); 3.1–3.9(m,6H); 4.2(q,2H); 4.4–4.9 (m,4H); 5.1(d,1H); 5.8(d,1H); 6.3–7.2(m,5H); 8.3(d,1H). |
| 3 | 1.25(t,3H); 3.3–3.6(m,2H); 4.25(q,2H); 4.6– 4.8(m,2H); 4.6–5.0(m,2H); 5.1(d,1H); 5.45 (m,2H); 5.8(d,1H); 6.4–6.8(m,3H); 6.95(s,1H); 7.15(d,1H); 7.5(d,2H); 7.9(d,2H); 8.4(d,1H); 9.05(s,1H). |
| 4 | 1.25(t,3H); 3.2–3.6(m,2H); 4.2(q,2H); 4.6–5.1 (m,4H); 5.1(d,1H); 5.5(s,2H); 5.8(d,1H); 6.4– 6.9(m,3H); 6.95(s,1H); 7.1–7.3(m,1H); 7.7 (d,2H); 8.2(d,2H); 8.2–8.4(m,1H); 9.1(m,1H). |
| 5 | 1.25(t,3H); 2.15(s,6H); 3.1–3.7(m,2H); 3.9 (s,3H); 4.2(q,2H); 4.5–4.9(m,4H); 5.1(d,1H); 5.8(d,1H); 6.95(s,1H); 7–7.4(m,5H); 8.2(d,2H). |
| 6 | 2.2(s,6H); 3.4(m,2H); 3.85(s,3H); 4.4–5.05 (m,6H); 5.1(d,1H); 5.8(d,1H); 7.05(s,1H); 7.1–7.6(m,4H); 8.4(m,1H); 8.9(s,1H). |
| 7 | 3.2–3.5(m,2H); 4.4–5.2(m,7H); 5.4(s,2H); 5.8(d,1H); 6.4–6.8(m,3H); 7.0–7.3(m,1H); 7.1(s,1H); 7.5(d,2H); 7.9(d,2H); 8.3– 8.6(m,1H); 9.0–9.2(m,1H). |
| 8 | 1.55(s,6H); 3.25–3.55(m,2H); 3.85(s,3H); 4.6– 5.0(m,4H); 5.15(d,1H); 5.85(d,1H); 6.4–7.5 (m,4H); 7.0(s,1H); 8.3(d,1H); 8.8(s,1H). |
| 9 | 1.55(s,6H); 3.2–3.5(m,2H); 4.5–5.0(m,4H); 5.1(d,1H); 5.4(s,2H); 5.85(d,1H); 6.4–6.8 (m,3H); 7.0(s,1H); 7.15(d,1H); 7.5(d,2H); 7.9(d,2H); 8.4(m,1H); 9.0(m,1H). |
| 10 | 1.45(d,3H); 3.2–3.5(m,2H); 3.9(s,3H); 4.6–5.0 (m,5H); 5.1(d,1H); 5.9(d,1H); 6.4–6.8(m,3H); 7.0(s,1H); 7.15(d,1H); 8.3(d,1H); 8.8(s,1H). |
| 11 | 1.5(d,3H); 3.3–3.6(m,2H); 4.6–5.2(m,5H); 5.2 (d,1H); 5.45(s,2H); 5.9(d,2H); 6.5–6.8(m,3H); 7.05(s,1H); 7.25(d,1H); 7.55(d,2H); 7.95 (d,2H); 8.45(m,1H); 9.1(m,1H). |
| 12 | 3.2–3.5(m,2H); 3.85(s,3H); 4.6–5.0(m,6H); 5.1 (d,1H); 5.8(d,1H); 6.4–6.8(m,3H); 7.1(s,1H); 7.15(d,1H); 8.3(d,1H); 8.8(s,1H). |
| 13 | 3.25–3.55(m,2H); 4.5–5.0(m,6H); 5.1(d,1H); 5.4 (s,2H); 5.8(d,1H); 6.3–6.8(m,3H); 7.0(s,1H); 7.15(d,1H); 7.5(d,2H); 7.9(d,2H); 8.4(d,1H); 9.05(m,1H). |
| 14 | 3.3–3.6(m,2H); 4.5–5.0(m,6H); 5.1(d,1H); 5.55 (s,2H); 5.8(d,1H); 6.4–6.8(m,3H); 7.0(s,1H); 7.2(d,1H); 7.65(d,2H); 8.2(d,2H); 8.4(m,1H); 9.05(m,1H). |
| 15 | 3.2–3.7(m,2H); 4.5–5.0(m,8H); 5.15(d,1H); 5.4(m,2H); 5.85(d,1H); 5.8–6.2(m,1H); 6.4– 6.8(m,3H); 7.1(s,1H); 7.2–7.4(m,2H); 8.3(d,2H). |
| 16 | 3.35–3.6(m,2H); 4.45–5.0(m,6H); 5.15(d,1H); 5.82(d,1H); 5.91(s,2H); 6.4–6.8(m,3H); 7.1(s,1H); 7.2–7.4(m,2H); 8.5(d,2H); |

TABLE II-continued

NMR data for the compounds of Examples 1-21 in DMSOd$_6$ + CD$_3$CO$_2$D + TFAd.

| Example No. | |
|---|---|
| | 9.3(s,1H). |
| 17 | 2.1(s,3H); 3.3–3.6(m,2H); 4.4–4.9(m,6H); 5.15(d,1H); 5.3(s,2H); 5.8(d,1H); 6.4–6.8(m,3H); 7.1(s,1H); 7.0–7.3(m,2H); 8.4(d,2H). |
| 18 | 1.25(t,3H); 3.2–3.7(m,2H); 4.25(q,2H); 4.55–4.9(m,4H); 5.2(d,1H); 5.85(d,1H); 5.95(s,2H); 6.4–6.8(m,3H); 7.0(s,1H); 7.2(m,2H); 8.4(d,2H); 9.3(s,1H). |
| 19 | 1.25(t,3H); 3.2–3.7(m,2H); 4.25(q,2H); 4.55–5.1(m,4H); 5.15(d,1H); 5.55(s,2H); 5.8(d,1H); 6.4–6.8(m,3H); 6.95(s,1H); 7.15(d,1H); 8.05(s,1H); 8.6(d,1H); 9.1(m,1H). |
| 20 | 1.25(t,3H); 3.3–3.6(m,2H); 4.25(q,2H); 4.6–5.05(m,4H); 5.15(d,1H); 5.55(s,2H); 5.85(d,1H); 6.4–6.8(m,3H); 6.95(s,1H); 7.2(d,1H); 8.35(s,1H); 8.5(d,1H); 9.0(m,1H). |
| 21 | 1.25(m,3H); 3.3–3.6(m,2H); 4.2(m,2H); 4.6–5.0(m,4H); 5.15(d,1H); 5.35(s,2H); 5.8(d,1H); 6.4–6.8(m,3H); 7.0(s,1H); 7.2(d,1H); 7.5(s,1H); 8.5(d,1H); 9.2(m,1H). |

EXAMPLE 22

7 [2-(2-aminothiazol-4-yl)-2 ((Z) 1-carboxy-1-methylethoxyimino) acetamido]-3-[N-(1-methyl-4-pyridinio) N-(2-(N'-3,4-diacetoxybenzoylamino) -ethyl)aminomethyl]ceph-3-em-4-carboxylic acid 3,4 diacetoxybenzoylchloride (37mg, 0.145mmol) was added in small portions to a solution of 7 [2 (2 aminothiazol-4 yl)-2 ((Z) 1-carboxy -1-methylethoxy-imino)acetamido]-3-[N-(1-methyl-4-pyridinio)-N-(2-amino)ethylaminomethyl]ceph-3-em-4-carboxylate (140 mg, 0.145 mmol) and TEA (0.081ml, 0.55mmol) in 10ml MeOH at room temperature with stirring. After 30 minutes at room temperature the mixture was neutralised by addition of AcOH and evaporated. The residue was purified by preparative HPLC, eluting with MeOH/AcOH/water 35/1/65, and the title compound (36mg) obtained after evaporation and lyophilisation NMR (DMSOd$_6$, AcOHd, TFA) 1.2(s,3H); 1.5(s,6H); 2.8(s,6H); 2.8–4.25(m,6H); 3.9(s,3H); 4.7(m,2H); 5.2(d,1H); 5.8(d,1H); 7.0(s,1H); 7.1–7.5(m,3H); 7.6(s,1H); 7.8(d,1H); 8.25(d,2H).

Preparation of starting materials

The cephalosporin starting materials detailed in Table III used in Examples 1-21 are novel compounds.

TABLE III

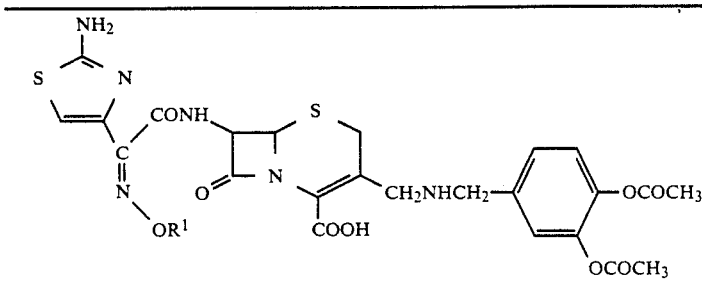

| Examples | —R1 | Yield % | Footnotes |
|---|---|---|---|
| 1-5, 18-21 | —Et | 36 | |
| 6,7, 15-17 | —CH$_2$CF$_3$ | 49 | |
| 8,9 | $\underset{CH_3}{\overset{CH_3}{{-}\!\!\!{+}\!\!\!{-}COOH}}$ | 23 | 1 |
| 10,11 | $\underset{H}{\overset{CH_3}{{-}\!\!\!{+}\!\!\!{-}COOH}}$ | 33 | 1 |
| 12-14 | —CH$_2$COOH | 32 | 1 |

The starting material for Examples 1-5 and 18-21 was prepared as follows:

To a solution of 3-aminomethyl-7-[2-(2-aminothiazol-4-yl)-2-((Z)-ethoxyimino)acetamido]ceph-3-em-4-carboxylic acid (320 mg) and 3,4-diacetoxy-benzaldehyde (190 mg) in MeOH (20 ml) and water (1 ml) maintained at pH 5.5–6.0 was added portionwise sodium cyanoborohydride (50 mg).

After 8 hours the mixture was evaporated to near-dryness and water (50 ml) was added to precipitate the produce, which was filtered and dried.

This generally process was also used to prepare the starting materials for Example 6-17. Some compounds (indicated by (Footnote 1) in the Table III) were further purified on a Diaion HP 20 SS resin column using MeOH/H$_2$O mixtures containing AcOH (1%).

NMR data for the above starting materials is given in Table IV.

TABLE IV

NMR data for starting materials of TABLE III in DMSOd$_6$ + CD$_3$CO$_2$D + TFAd.

| Starting material for Examples | |
|---|---|
| 1-5, 18-21 | 1.3(t,3H); 2.25(s,6H); 3.5–3.9(m,2H); 3.9–5.1(m,2H); 4.2(s,2H); 4.25(q,2H); 5.2(d,1H); 5.9(d,1H); 7.0(s,1H); 7.1–7.6(m,3H). |
| 6,7, 15-17 | 2.25(s,6H); 3.5–3.9(m,2H); 3.9–4.1(m,2H); 4.25(s,2H); 4.8(q,2H); 5.15(d,1H); 5.9 |

TABLE IV-continued

NMR data for starting materials of TABLE III in DMSOd$_6$ + CD$_3$CO$_2$D + TFAd.

| Starting material for Examples | |
|---|---|
| | (d,1H); 7.1(s,1H); 7.2–7.6(m,3H). |
| 8,9 | 1.55(s,6H); 2.2(s,6H); 3.5–3.8(m,2H); 3.8–4.0(m,2H); 4.15(s,2H); 5.1(d,1H); 5.9(d,1H); 7.05(s,1H); 7.05–7.5(m,3H). |
| 10,11 | 1.5(d,3H); 2.25(s,6H); 3.6–3.8(m,2H); 3.8–4.1(m,2H); 4.2(s,2H); 4.8(q,1H); 5.2(d,1H); 5.9(d,1H); 7.05(s,1H), 7.1–7.5(m,3H). |
| 12–14 | 2.25(s,6H); 3.6–3.8(m,2H); 3.8–4.1(m,2H); 4.2(s,2H); 4.75(s,2H); 5.2(d,1H); 5.9(d,1H); 7.2(s,1H); 7.3–7.5(m,3H). |

The heterocyclic starting materials are known from, or prepared by methods similar to those of, the literature. In particular reference is made to EP-A 127992 and EP-A 164944.

In general the appropriate chloromethyl heterocycle was mixed with 4 methylthio pyrimidine or 4 methylthiopyridine, either without solvent or in a polar solvent such as methanol, The mixture was heated to 100° C., and on completion of reaction, the mixture was cooled and the product precipitated. These crude products were either used in that state or were purified on a HP20SS resin column. The products could be characterised by NMR for example: (DMSO-d$_6$/CD$_3$CO$_2$D/TFA-d$_6$)

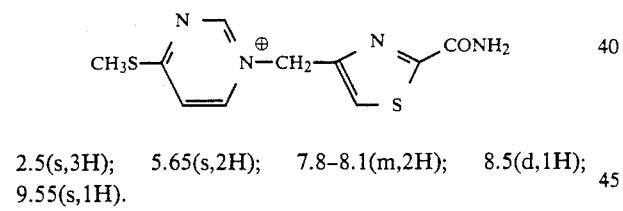

2.5(s,3H); 5.65(s,2H); 7.8–8.1(m,2H); 8.5(d,1H); 9.55(s,1H).

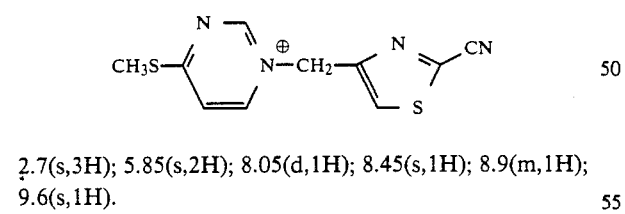

2.7(s,3H); 5.85(s,2H); 8.05(d,1H); 8.45(s,1H); 8.9(m,1H); 9.6(s,1H).

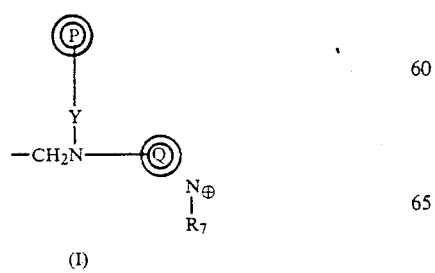

(I)

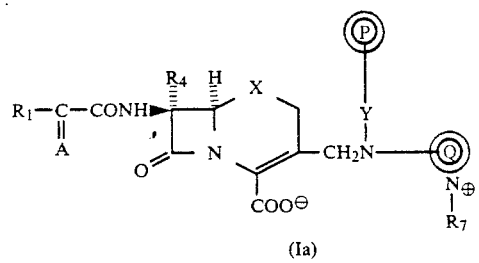

(Ia)

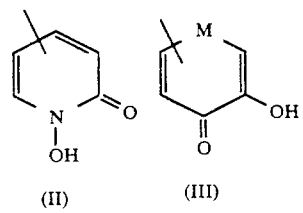

(II)    (III)

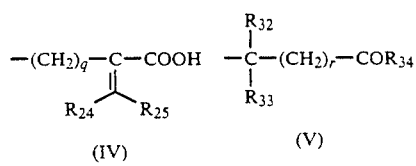

(IV)    (V)

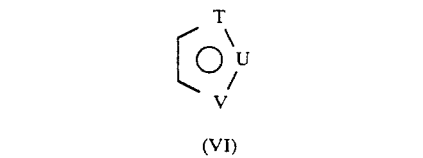

(VI)

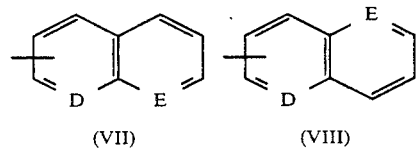

(VII)    (VIII)

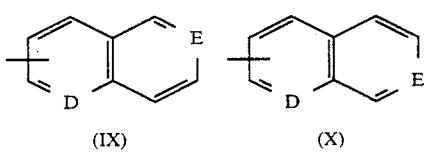

(IX)    (X)

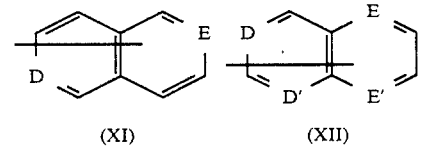

(XI)    (XII)

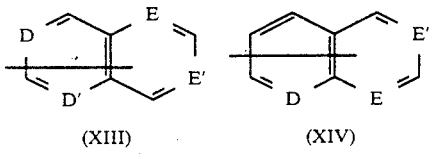

(XIII)    (XIV)

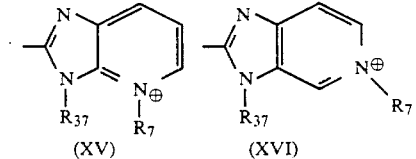

(XV)    (XVI)

-continued

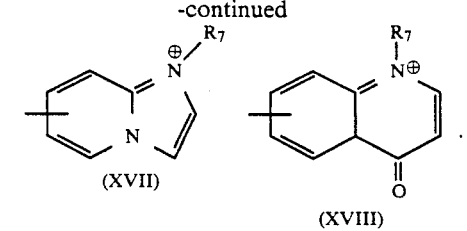

(XVII)  (XVIII)

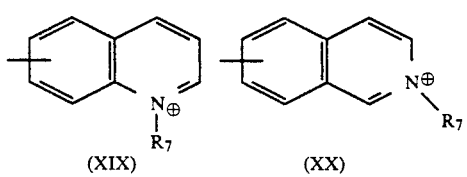

(XIX)  (XX)

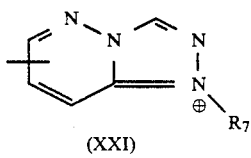

(XXI)

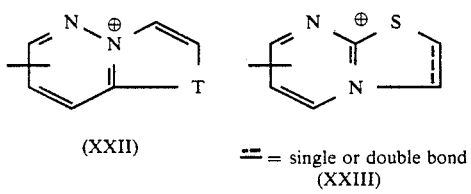

(XXII)  == = single or double bond
(XXIII)

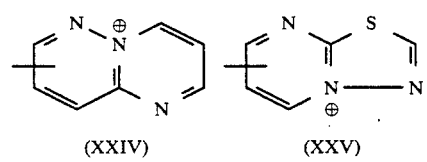

(XXIV)  (XXV)

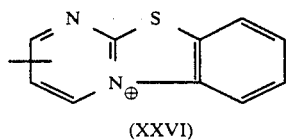

(XXVI)

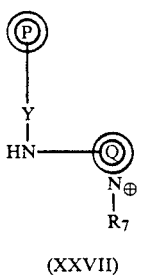 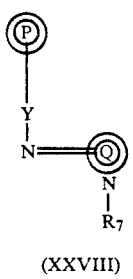

(XXVII)  (XXVIII)

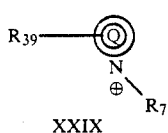

XXIX

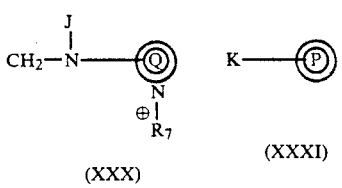

(XXX)  (XXXI)

-continued

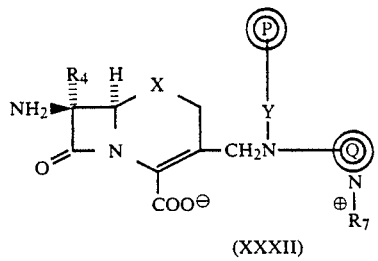

(XXXII)

$$R_1.C.COOH$$
$$\phantom{R_1.C.}A$$

(XXXIII)

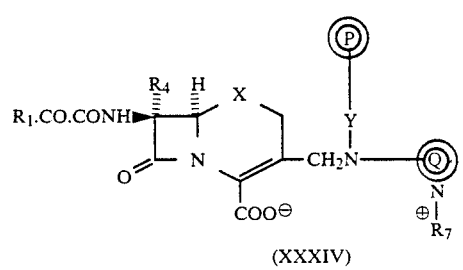

(XXXIV)

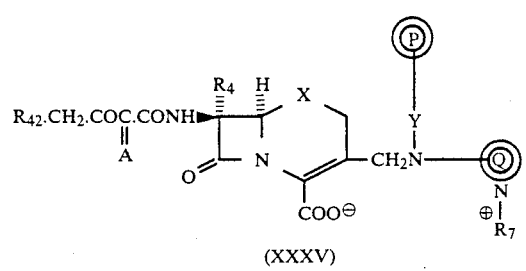

(XXXV)

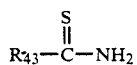

(XXXVI)

What is claimed is:

1. A cephalosporin compound of the formula (Ia):

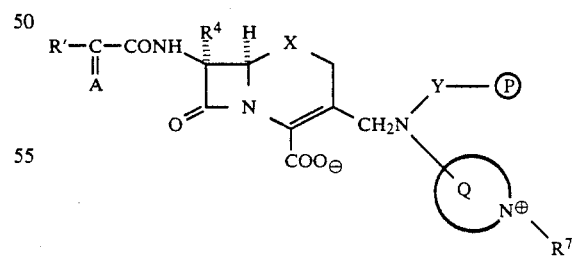

wherein:
X is sulphur or sulphinyl;
$R^1$ is 2-aminothiazol-4-yl or 2-aminooxazol-4-yl each optionally substituted in the 5-position by fluorine, chlorine or bromine, or $R^1$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

A is of the formula =NOR² (having the syn configuration about the double bond) wherein R2 is hydrogen, (1-6C)alkyl, (3-8C)cycloalkyl, (1-3C)alkyl(-3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, di(1-4C)alkyl-carbamoyl(1-4C)alkyl, (1-4C)haloalkylcarbamoyl (1-4C)-alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkane-sulphonyl(1-4-C)alkyl, amino(2-6C)alkyl, azido(2-6C)alkyl, ureido(2-6C)alkyl, (1-4C)-alkylamino(1-6C)alkyl, (2-8C)dialkylamino(2-6C) alkyl, (1-5C)cyanoalkyl, 3-amino-3-carboxypropyl, 2-(amidino)ethyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or —R2 may be of the formula IV:

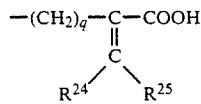

in which q is 1 or 2 and R24 and R25 are hydrogen or (1-4C)alkyl, or —R2 may be of the formula V:

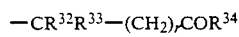

in which r is 0-3, R32 is hydrogen, (1-3C)alkyl or methylthio, R33 is hydrogen, (1-3C)alkyl, (3-7C)cycloalkyl, cyano, carboxy, (2-5C)carboxyalkyl or methanesulphonylamino, or R32 and R33 are joined to form, together with the carbon to which they are attached, a (3-7C)carbocyclic ring, and R34 is hydroxy, amino, (1-4C)alkoxy, (1-4C) alkylmino, or of the formula NHOR35 in which R35 is hydrogen or (1-4C)alkyl;

or A may be of the formula =CH.R3 wherein R3 is hydrogen, halogen, (1-6C)alkyl, (3-7C)cycloalkyl, (2-6C)alkenyl, (3-7C)cycloalkenyl, phenyl or benzyl;

R⁴ is hydrogen, methoxy or formamido;

Q is a 5 or 6 membered ring containing NR⁷ and 0 to 3 further heteroatoms selected from nitrogen, oxygen and sulphur and optionally fused on an available carbon-carbon or carbon-nitrogen bond to a benzene ring or a ring of the formula (VI):

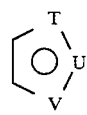

wherein T, U and V are selected from oxygen, sulphur, nitrogen, carbon, —NH— and —CH—;
or ring Q is of the formula VII–XXVI:

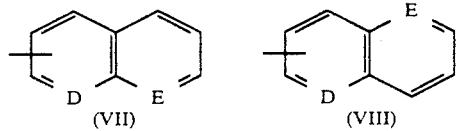
(VII) (VIII)

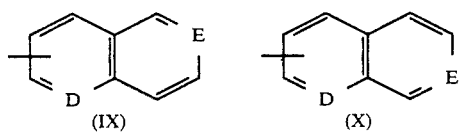
(IX) (X)

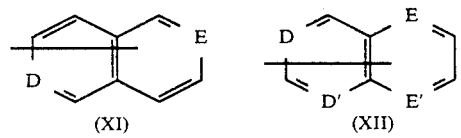
(XI) (XII)

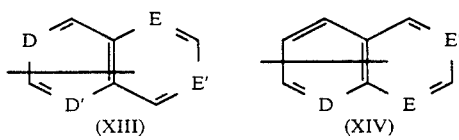
(XIII) (XIV)

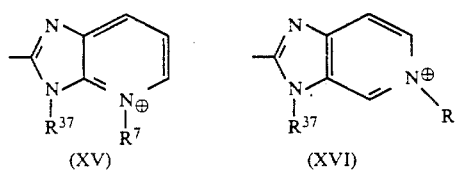
(XV) (XVI)

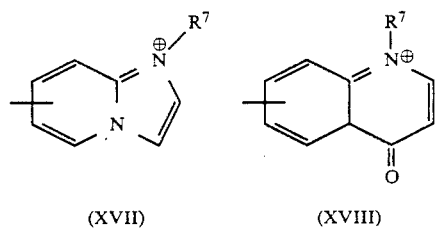
(XVII) (XVIII)

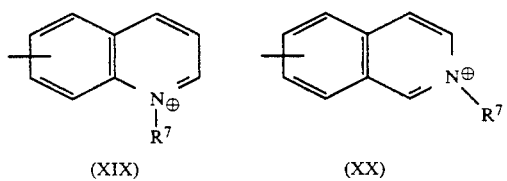
(XIX) (XX)

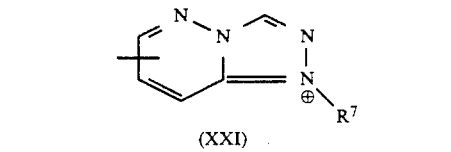
(XXI)

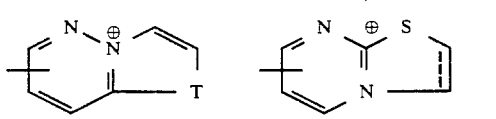
(XXII) (XXIII)

== = Single or double bond

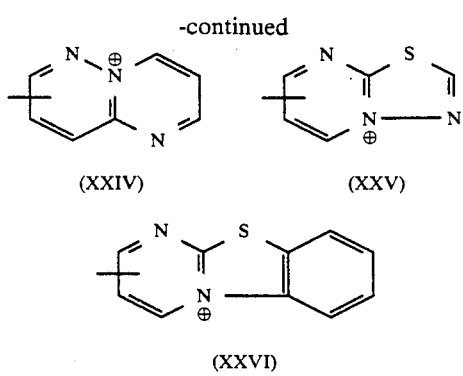

(XXIV)  (XXV)

(XXVI)

wherein one of D, D¹, E and E¹ represents NR⁷ and the remainder represent uncharged nitrogen atoms and R³⁷ represents hydrogen or a group R⁶ (as hereinafter defined);

Ring Q and the rings VI-XXVI being optionally substituted by at least one group R⁵ or R⁶ (as hereinafter defined);

on a carbon atom or atoms available for substitution by 1,2 or 3 groups R5 wherein R5 is halogen, (1-6C)alkyl, carboxy, (2-6C)alkoxycarbonyl, (2-6C)alkoxycarbonyl(1-4C)alkyl, (1-6C)-alkoxy, (1-6C)alkylthio, cyano, (1-4C)cyanoalkyl, amino, (1-6C)-alkylamino, (2-8C)dialkylamino, phenyl(1-4C)alkylamino, nitrophenyl(1-4C)alkylamino, (3-6C)alkenylamino, amino(1-6C)alkylamino, (1-6C)alkoxy(1-6C)alkylamino, hydroxy(1-6C)alkylamino, hydroxy, mercapto, carbamoyl, (2-6C)alkylcarbamoyl, (3-10C)dialkylcarbamoyl, phenylthio and heteroarylthio (wherein heteroaryl is furan, thiophene, imidazole, thiazole, pyrazole, thiadiazole, pyridine, pyrimidine, pyrazine or pyrimidine) wherein when more than one group R5 is present these may be the same or different;

on an uncharged nitrogen atom available for substitution by a group R6 wherein R6 is (1-6C)alkyl, phenyl or benzyl;

R7 is hydrogen, (1-6C)alkyl (optionally substituted by carboxy, (1-6C)alkoxycarbonyl, carbamoyl, mono- or di-(1-4C)alkylcarbamoyl, hydroxy, (1-4C)alkoxy, amino, mono- or di-(1-4C)alkyamino, (1-4C)alkanoyl, benzoyl, cyano, carboxyaminocarbonyl, (1-6C)alkoxycarbonylaminocarbonyl, (1-4C)alkoxy(2-4C)alkoxy or phenyl), (1-6C)alkoxy, phenyl(1-6C)alkoxy, amino, (1-6C)alkylamino, (3-6C)cycloalkyl, (3-6C)cycloalkenyl, cyano(3-6C)cycloalkenyl, (2-6C)alkenyl (optionally substituted by (1-6C)alkyl, halogen, cyano, carbamoyl, mono- or di-(1-4C)alkylcarbamoyl, piperidinocarbonyl or morpholinocarbonyl), 2-ureidoethyl, 2-thioureidoethyl, 2-(thioacetylamino)-ethyl, sulphamoyl, 2-amino-2-carboxyethyl, acetylaminomethyl, phthalimidomethyl, 4-5-dihydro-imidazol-2-ylmethyl, 3,4,5,6-tetrahydropyrimidin-2-ylmethyl, 2-(1,2,3,6-tetrahydro-2,6-dioxopurin-7-yl)ethyl, 2-hydroxyiminopropyl (syn or anti) [(1-4C)alkoxyimino]propyl (syn or anti) or phenyl, or R7 is of the formula —(CH₂)₂—NR8R9R10 in which R8, R9 and R10 are (1-4C)alkyl, or R7 is of the formula —(CH₂)ₛ—R11 in which s is 0-2 and R11 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C)alkyl]tetrazole, furan, thiophene, pyrrole, 1-[(1-4C)alkyl]pyrrole, oxazole, thiazole, imidazole, 1-[1-4C)alkyl]imidazole, isoxazole, isothiazole, pyrazoke, 1,2,3-thiadiazoke, 1-[1-4C)alkyl]pyrazole, benzfuran, benzthiophene, indole, oxindole, 1-[(1-4C)alkyl]indole, benzoxazole, benzthiazole, benzimidazole, 1-[(1-4C)alkyl]benzimidazole, or 3,4-dihydro-4-oxo-2H-benzo[e]oxazine (each of these ring systems being linked to (CH₂)ₛ through carbon and each ring system being optionally substituted by halogen, (1-6C)alkyl, (1-4C)haloalkyl, (3-6C)cycloalkyl, (3-6C)cycloalkyl(1-4C)alkyl, (2-6C)alkenyl, carboxy, (2-6C)alkoxycarbonyl, (1-6C)alkoxy, cyano, (2-6C)-cyanoalkenyl, carbamoyl, mono-or di-(1-4-C)alkyl-carbamoyl, (1-4C)alkanoylamino, guanidino, hydroxy, nitro or amino), or R7 is 2-guanidino-thiazole-4-ylmethyl, hydroxybenzoylmethyl, 2-thenyl, 2-imidazolylmethyl or cinnamyl (each optionally substituted by halogen, nitro or carbamoyl), or R7 is —(CH₂)ₜNHCOR12 or —(CH₂)ₜS(O)ᵤ—R12 in which t is 1-6, u is 0, 1 or 2 and R12 is (1-6C)alkyl or (1-6C)alkoxy, or R7 is of the formula (CH₂)₂N=CR13NR14R15 or (CH₂)ᵥC(=NR13)NR14R15 or a tautomer thereof in which v is 1-6 and R13, R14, R15 are hydrogen or (1-4C)alkyl, (wherein when R7 is or contains a phenyl group, the phenyl group is optionally substituted by 1 or 2 groups selected from halogen, (1-6C)alkyl, (1-6C)alkoxy, amino, carboxy, nitro, carbamoyl, cyano, trifluoromethyl, aminomethyl, (1-4C)alkanoyl, (1-4C)-alkanoylamino, halo(1-4C)alkyl, (2-6C)alkoxycarbonyl, mono- or di-(1-4C)alkylcarbamoyl, mesyl, vinyl, sulpho, sulphamoyl or mono- or di(-1-4C)alkylsulphamoyl) or when the positively charged nitrogen atom occurs at the junction between fused rings R7 is absent;

Y is straight or branched (1-6C)alkylene optionally substituted by cyano, carboxy, (1-4C)alkoxycarbonyl, nitro, halogen, carbamoyl, mono- or di-(1-4C-)alkylcarbamoyl or trifluoromethyl; or Y is —CH₂CH₂NHCO— or a bond;

P represents:

(i) a benzene ring optionally fused to a further benzene ring (so forming a naphthyl group) said ring system substituted by groups W and Z which are ortho with respect to one another wherein W is hydroxy or an in vivo hydrolysable ester thereof and Z is hydroxy or an in vivo hydrolysable ester thereof;

ring system P optionally being further substituted by (1-4C)alkyl, halogen, hydroxy, cyano, trifluoromethyl, nitro, amino, mono- or di-(1-4C)alkylamino, formyl, (1-4C)alkanoyl, (1-4C)alkoxy, (1-4C)alkylthio, (1-4C)alkanoyloxy, carbamoyl or mono- or di(1-4C)alkylcarbamoyl;

and the N-oxides thereof where chemically possible; and pharmaceutically acceptable salts thereof.

2. A compound according to claim 1 wherein ring Q represents a pyridine or pyrimidine ring or a pyridine or pyrimidine ring fused to either a benzene ring or thienyl group.

3. A compound according to claim 1 wherein X is sulphur and R is hydrogen.

4. A compound according to claim 1 wherein R¹ is 2-aminothiazole-4-yl and A is a group =NOR² wherein $R^2$ is $C_{1-6}$alkyl, 1-carboxy($C_{3-7}$)cycloalkyl or 2-carboxyprop-2-yl.

5. A compound according to claim 1 wherein Y is —$CH_2$—.

6. An antibacterial pharmaceutical composition which comprises an antibacterially effective amount of a compound according to claim 1 and a pharmaceutically acceptable carrier.

7. A method of treating a bacterial infection in a mammal comprising administering to a mammal in need of such treatment an antibacterially effective amount of a compound according to claim 1.

* * * * *